US011963785B2

(12) United States Patent
Franz et al.

(10) Patent No.: US 11,963,785 B2
(45) Date of Patent: Apr. 23, 2024

(54) METHODS, SYSTEMS, AND COMPUTER READABLE MEDIA FOR UTILIZING VISUOMOTOR ERROR AUGMENTATION FOR BALANCE REHABILITATION

(71) Applicant: The University of North Carolina at Chapel Hill, Chapel Hill, NC (US)

(72) Inventors: Jason Roy Franz, Durham, NC (US); Mu Qiao, Ruston, LA (US)

(73) Assignee: THE UNIVERSITY OF NORTH CAROLINA AT CHAPEL HILL, Chapel Hill, NC (US)

( * ) Notice: Subject to any disclaimer, the term of this patent is extended or adjusted under 35 U.S.C. 154(b) by 498 days.

(21) Appl. No.: 17/202,989

(22) Filed: Mar. 16, 2021

(65) Prior Publication Data
US 2021/0282699 A1 Sep. 16, 2021

Related U.S. Application Data

(60) Provisional application No. 62/990,417, filed on Mar. 16, 2020.

(51) Int. Cl.
A61B 5/00 (2006.01)
A61B 5/11 (2006.01)
A63B 26/00 (2006.01)
A63B 71/06 (2006.01)

(52) U.S. Cl.
CPC ............ A61B 5/4023 (2013.01); A61B 5/112 (2013.01); A63B 26/003 (2013.01); A63B 71/0622 (2013.01); A61B 2505/09 (2013.01); A63B 2071/0638 (2013.01); A63B 2071/0644 (2013.01)

(58) Field of Classification Search
CPC ... A61B 5/112; A61B 5/4023; A61B 2505/09; A63B 26/003; A63B 71/0622; A63B 2071/0638; A63B 2071/0644; G06T 15/00–87; G06T 19/006; G06T 11/00
See application file for complete search history.

(56) References Cited

PUBLICATIONS

Franz, Jason R., et al. "Advanced age brings a greater reliance on visual feedback to maintain balance during walking." Human movement science 40 (2015): 381-392. (Year: 2015).*

(Continued)

Primary Examiner — Daniel F Hajnik
(74) Attorney, Agent, or Firm — Jenkins, Taylor & Hunt, P.A.

(57) ABSTRACT

Methods, systems, and computer readable media for utilizing visuomotor error augmentation for balance rehabilitation are provided. An exemplary method includes displaying a dynamic virtual environment defined by an optical flow, obtaining position data of an anatomical portion of a subject that is virtually traversing the dynamic virtual environment, and using the position data to determine a mediolateral displacement measurement of the subject. The method further includes utilizing the mediolateral displacement measurement to define feedback control loop data, establishing an augmented visual error that dynamically adjusts the dynamic virtual environment, wherein the augmented visual error is based on the feedback control loop data and a predefined visual gain factor, and adjusting the optical flow of the dynamic virtual environment by using the augmented visual error.

17 Claims, 9 Drawing Sheets

(56) References Cited

PUBLICATIONS

Anson et al., "Does visual feedback during walking result in similar improvements in trunk control for young and older healthy adults?" Journal of Neuro Engineering and Rehabilitation, vol. 10, No. 110, pp. 1-18 (2013).

Cowan et al., "The Critical Role of Locomotion Mechanics in Decoding Sensory Systems," Journal of Neuroscience, vol. 27, No. 5, pp. 1123-1128 (Jan. 2007).

Cramer et al., "Hidden multiplicity in exploratory multiway ANOVA: Prevalence and remedies," Psychonomic Bulletin & Review, vol. 23, pp. 640-647 (2016).

Dingwell et al., "Re-interpreting Detrended Fluctuation Analyses of Stride-to-Stride Variability in Human Walking," Gait & Posture, vol. 32, No. 3, pp. 348-353 (Jul. 2010).

Franz et al., "Visuomotor Entrainment and the Frequency-Dependent Response of Walking Balance to Perturbations." IEEE Transactions on Neural Systems and Rehabilitation Engineering, vol. 25, No. 8, pp. 1135-1142 (Aug. 2017).

Grabiner et al., "Task-Specific Training Reduces Trip-Related Fall Risk in Women," Medicine & Science in Sports & Exercise, vol. 44, No. 12, pp. 2410-2414 (2012).

Hayhoe et al., "The role of binocular vision in walking," Visual Neuroscience, vol. 26, No. 1, pp. 73-80 (2009).

Hilliard et al., "Lateral Balance Factors Predict Future Falls in Community-Living Older Adults," Archives of Physical Medicine and Rehabilitation, vol. 89, No. 9, pp. 1708-1713 (Sep. 2008).

Hurt et al., "Variation in trunk kinematics influences variation in step width during treadmill walking by older and younger adults," Gait & Posture, vol. 31, pp. 461-464 (2010).

Kiemel et al., "Identification of Neural Feedback for Upright Stance in Humans: Stabilization Rather Than Sway Minimization," Journal of Neuroscience, vol. 31, No. 42, pp. 15144-15153 (Oct. 2011).

McAndrew et al., "Walking variability during continuous pseudo-random oscillations of the support surface and visual field," Journal of Biomechanics, vol. 43, No. 8, pp. 1-14 (May 2010).

O'Connor et al., "Direction-Dependent Control of Balance During Walking and Standing," Journal of Neurophysiology, vol. 102, 1411-1419, (Jun. 2009).

Patton et al., "Visuomotor Learning Enhanced by Augmenting Instantaneous Trajectory Error Feedback During Reaching," PLoS One, vol. 8, No. 1, pp. 1-7 (Jan. 2013).

Peterka, R. J. "Sensorimotor Integration in Human Postural Control," Journal of Neurophysiology, vol. 88, pp. 1097-1118 (May 2002).

Peterka et al., "Dynamic Regulation of Sensorimotor Integration in Human Postural Control," Journal of Neurophysiology, vol. 91, pp. 410-423 (Sep. 2003).

Peterson et al., "Transient visual perturbations boost short-term balance learning in virtual reality by modulating electrocortical activity," Journal of Neurophysiology, vol. 120, pp. 1998-2010. https://doi.org/10.1152/jn.00292.2018 (Jul. 2018).

Qiao et al., "Aging effects on leg joint variability during walking with balance perturbations," Gait & Posture, vol. 62, pp. 27-33 (2018).

Qiao et al., "Does local dynamic stability during unperturbed walking predict the response to balance perturbations: An examination across age and falls history," Gait & Posture, vol. 62, pp. 1-16 (May 2018).

Richards et al., "Time-dependent tuning of balance control and aftereffects following optical flow perturbation training in older adults," Journal of Neuroengineering and Rehabilitation, vol. 16, No. 81, pp. 1-11 (2019).

Ros et al. "Optic flow stabilizes flight in ruby-throated hummingbirds," Journal of Experimental Biology, vol. 219, pp. 2443-2448 (2016).

Sinitksi et al., "Effects of perturbation magnitude on dynamic stability when walking in destabilizing environments," Journal of Biomechanics, vol. 45, pp. 2084-2091 (2012).

Terry et al., "Amplitude effects of medio-lateral mechanical and visual perturbations on gait," Journal of Biomechanics, vol. 45, pp. 1979-1986 (2012).

Thompson et al., "Do kinematic metrics of walking balance adapt to perturbed optical flow?" Human Movement Science, vol. 54, pp. 34-40 (2017).

Tseng et al., "Sensory prediction errors drive cerebellum-dependent adaptation of reaching," Journal of Neurophysiology, vol. 98, pp. 1-37 (May 2007).

Warren et al., "Direction of self-motion is perceived from optical-flow," Nature, vol. 336, pp. 1-3 (1988).

Warren et al., "Visual Control of Posture During Walking: Functional Specificity," Journal of Experimental Psychology: Human Perception and Performance, vol. 22, No. 4, pp. 818-838 (1996).

Wilkie et al., "Using vision to control locomotion: looking where you want to go," Experimental Brain Research, vol. 204, pp. 539-547 (2010).

Miall et al., "Forward Models for Physiological Motor Control," Neural Networks, vol. 9, pp. 1265-1279 (Mar. 1996).

Zeni et al., "Two simple methods for determining gait events during treadmill and overground walking using kinematic data," Gait & Posture, vol. 27, No. 4, pp. 1-9 (May 2008).

* cited by examiner

METHODS, SYSTEMS, AND COMPUTER READABLE MEDIA FOR UTILIZING VISUOMOTOR ERROR AUGMENTATION FOR BALANCE REHABILITATION

CROSS-REFERENCE TO RELATED APPLICATIONS

This application claims the priority benefit of U.S. Provisional Patent Application Ser. No. 62/990,417 filed Mar. 16, 2020, the disclosure of which is incorporated by reference herein in the entirety.

GOVERNMENT INTEREST

This invention was made with government support under Grant No. AG054797 awarded by the National Institutes of Health. The government has certain rights in the invention.

TECHNICAL FIELD

The subject matter described herein relates to the rehabilitative uses of virtual environments and associated measured sensory responses. More particularly, the subject matter described herein relates to methods, systems, and computer readable media for utilizing visuomotor error augmentation for balance rehabilitation.

SUMMARY

According to one aspect, the subject matter described herein relates to methods, systems, and computer readable media for utilizing visuomotor error augmentation for balance rehabilitation. An exemplary method includes displaying a dynamic virtual environment defined by an optical flow, obtaining position data of an anatomical portion of a subject that is virtually traversing the dynamic virtual environment, and using the position data to determine a mediolateral displacement measurement of the subject. The method further includes utilizing the mediolateral displacement measurement to define feedback control loop data, establishing an augmented visual error that dynamically adjusts the dynamic virtual environment, wherein the augmented visual error is based on the feedback control loop data and a predefined visual gain factor, and adjusting the optical flow of the dynamic virtual environment by using the augmented visual error.

In one example of the method, the dynamic virtual environment includes a virtual hallway.

In one example of the method, a foreground mediolateral position of the dynamic virtual environment is adjusted by the augmented visual error.

In one example of the method, the mediolateral displacement measurement is based on a difference of a mediolateral position of the dynamic virtual environment and a mediolateral position marker of the subject.

In one example of the method, the anatomical portion of the subject corresponds to at least one of a seventh cervical vertebrae of the subject, a global head position of the subject, and a global trunk position of the subject.

In one example of the method, augmented visual error defines a difference between a virtual perception of trunk motion of the subject and an actual trunk motion of the subject.

In one example of the method, the method further includes moving a foreground of the dynamic virtual environment based on the feedback control loop data and the augmented visual error by a value of G.

One exemplary system includes a display device configured to display a dynamic virtual environment defined by an optical flow and at least one position sensor device configured to obtain position data of an anatomical portion of a subject that is virtually traversing the dynamic virtual environment. The system further includes a system controller device configured to use the position data to determine a mediolateral displacement measurement of the subject, utilize the mediolateral displacement measurement to define feedback control loop data, establish an augmented visual error that dynamically adjusts the dynamic virtual environment, wherein the augmented visual error is based on the feedback control loop data and a predefined visual gain factor, and adjust the optical flow of the dynamic virtual environment by using the augmented visual error.

In one example of the system, the dynamic virtual environment includes a virtual hallway.

In one example of the system, a foreground mediolateral position of the dynamic virtual environment is adjusted by the augmented visual error.

In one example of the system, the mediolateral displacement measurement is based on a difference of a mediolateral position of the dynamic virtual environment and a mediolateral position marker of the subject.

In one example of the system, the anatomical portion of the subject corresponds to at least one of a seventh cervical vertebrae of the subject, a global head position of the subject, and a global trunk position of the subject.

In one example of the system, augmented visual error defines a difference between a virtual perception of trunk motion of the subject and an actual trunk motion of the subject.

In one example of the system, the system controller device is further configured to move a foreground of the dynamic virtual environment based on the feedback control loop data and the augmented visual error by a value of G.

The subject matter described herein may be implemented in hardware, software, firmware, or any combination thereof. As such, the terms "function" "node" or "engine" as used herein refer to hardware, which may also include software and/or firmware components, for implementing the feature being described. In one exemplary implementation, the subject matter described herein may be implemented using a computer readable medium having stored thereon computer executable instructions that when executed by the processor of a computer control the computer to perform steps. Exemplary computer readable media suitable for implementing the subject matter described herein include non-transitory computer-readable media, such as disk memory devices, chip memory devices, programmable logic devices, and application specific integrated circuits. In addition, a computer readable medium that implements the subject matter described herein may be located on a single device or computing platform or may be distributed across multiple devices or computing platforms.

BRIEF DESCRIPTION OF THE DRAWINGS

The subject matter described herein will now be explained with reference to the accompanying drawings of which.

DETAILED DESCRIPTION

Figure 1:
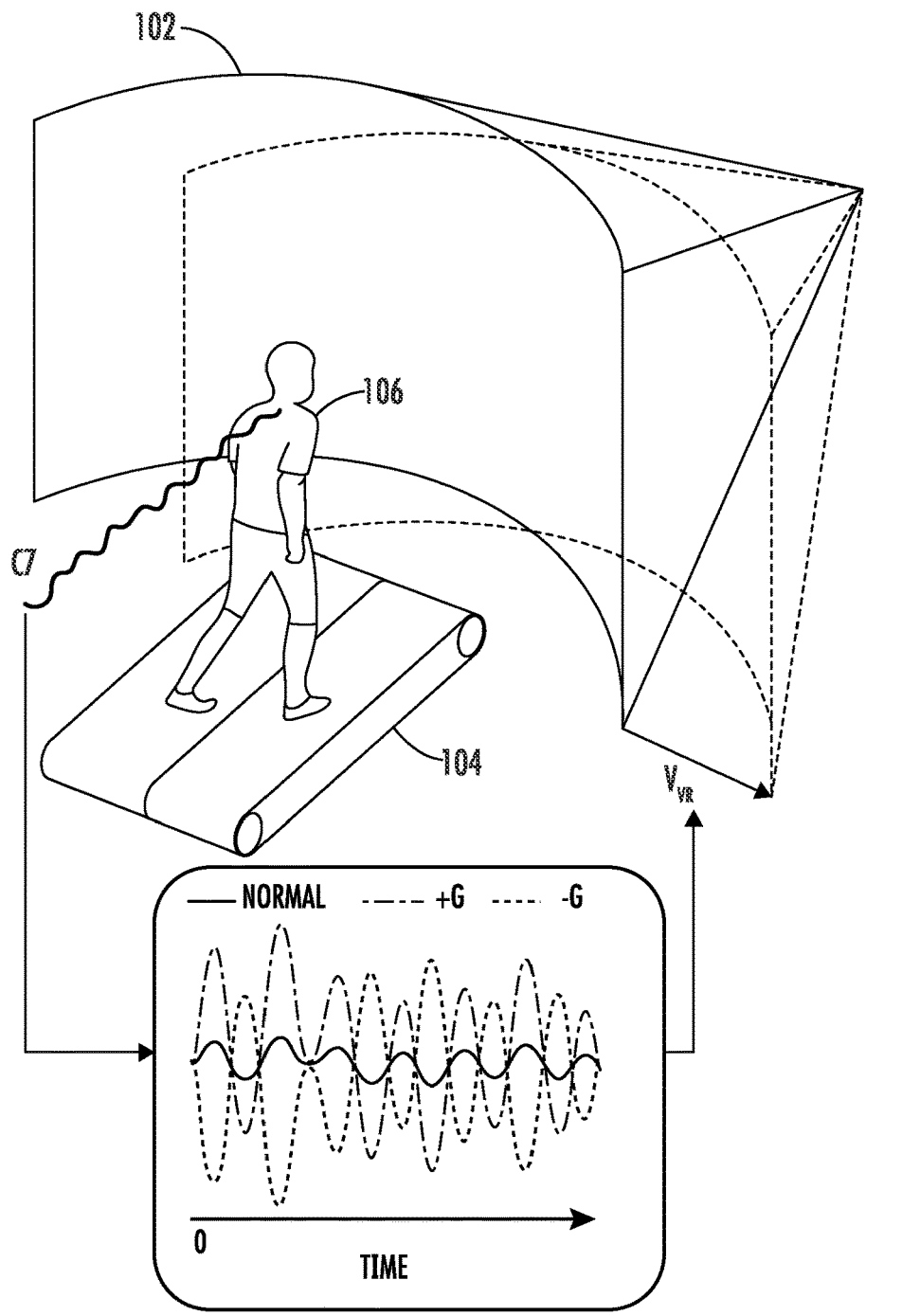
FIG. 1 illustrates a diagram of an exemplary system for utilizing visuomotor error augmentation for balance rehabilitation according to an embodiment of the subject matter described herein.
Figure 1:
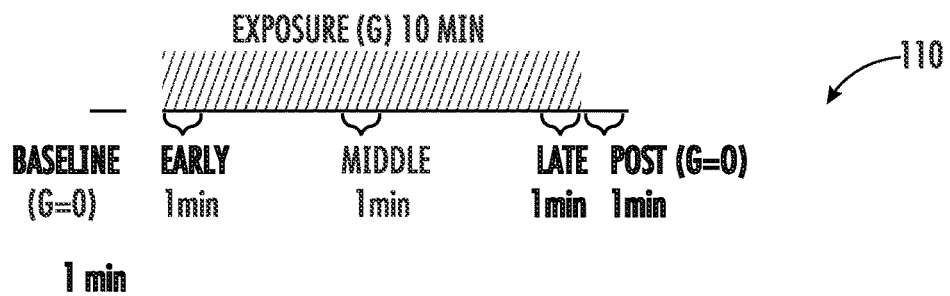

Prior work demonstrates that humans spontaneously synchronize their head and trunk kinematics to a broad range of driving frequencies of perceived mediolateral motion prescribed using optical flow. Using a closed-loop visuomotor error augmentation task in an immersive virtual environment, it was sought to understand whether unifying visual feedback with vestibular and somatosensory feedback is a control goal during human walking, at least in the context of head and trunk stabilization. It was hypothesized that humans would minimize visual errors during walking—i.e., those between the visual perception of movement and actual movement of the trunk. Notably, subjects did not minimize errors between the visual perception of movement and actual movement of the head and trunk. Rather, subjects increased mediolateral trunk range of motion in response to error-augmented optical flow with positive feedback gains. The results are more consistent with the alternative hypothesis—that visual feedback can override other sensory modalities and independently compel adjustments in head and trunk position. Also, aftereffects following exposure to error-augmented optical flow included longer, narrower steps and reduced mediolateral postural sway, particularly in response to larger amplitude positive feedback gains. The results allude to a recalibration of head and trunk stabilization toward more tightly regulated postural control following exposure to error-augmented visual feedback. Lasting reductions in mediolateral postural sway may have implications for using error-augmented optical flow to enhance the integrity of walking balance control through training, for example in older adults and any person with balance deficits, including neurodegenerative disease (e.g., Multiple sclerosis). Indeed, any population with peripheral sensation loss and/or unreliable distal sensation could benefit from the disclosed subject matter.

1. INTRODUCTION

Humans regulate lateral balance in walking through coordinated adjustments between the continuous control of posture (i.e., head and trunk stabilization) and the discrete (step-to-step) control of foot placement (i.e., step width). Here, successful coordination depends on appropriate motor planning and execution, which in turn depend on having accurate and reliable sensory feedback. Optical flow perturbations, a class of experimental paradigms used in the study of walking balance control, are unique in that they exclusively target that sensory feedback through the visual perception of lateral imbalance. Somewhat surprisingly, walking balance is acutely susceptible to those perturbations, and the resulting motor responses may have the capacity to inform how sensory feedback is used in the planning and execution of stable locomotion. For example, head and trunk kinematics during walking spontaneously synchronize (i.e., entrain) to a broad range of driving frequencies of perceived mediolateral (ML) motion prescribed using optical flow. The intuitive interpretation of those findings is that such entrainment may act to minimize errors between the visual perception of motion and the actual motion of the head and trunk, thereby unifying visual with vestibular and somatosensory feedback. However, direct evidence that minimizing these "visual errors" is a control goal for head and trunk stabilization during human walking is currently lacking.

Head and trunk stabilization is critical for regulating walking balance. Usually thought of as arising from corrective motor responses governed by vestibular feedback, this process is more likely governed by the integration of sensory cues from both visual and vestibular feedback. For example, while vestibular feedback provides a spatial reference for effective head and trunk stabilization during walking, such stabilizing also provides a reliable visual reference for regulating foot placement, navigating complex environments, and avoiding obstacles. In addition, postural deviations that occur normally in walking influence not only the spatial reference for head and trunk stabilization but also optical flow—the visual perception of self-motion, the relative motion of objects in the environment, or both. Indeed, some studies have shown evidence that visual feedback, and optical flow, in particular, play an important role in both postural stability and navigation during walking. However, it remains unclear how this visual perception of self-motion, in concert with cues from other sensory modalities, is integrated to stabilize the head and trunk during walking—knowledge with particular relevance to navigating unstable environments that could challenge walking balance.

In the neural control of movement, sensory errors arise when actual sensory feedback cues differ from those anticipated to follow from a given motor command. Also, on-line monitoring of sensory errors can independently drive motor corrections, for example, decreasing the difference between the visual perception of movement and actual movement of the limb during an arm reaching task. Different from the optical flow perturbations used to study entrainment, error-augmentation is tied to the subjects' own performance and is thus more analogous to a biofeedback paradigm. In walking, a similar process of error minimization could provide a logical explanation for why people synchronize (i.e., entrain) their head and trunk movements to even very complex mediolateral optical flow oscillations. Specifically, the onset of such oscillations, for example in the context of optical flow perturbation studies, introduces errors between the visual perception of self-motion and the actual motion of the head and trunk. Indeed, it was previously proposed that the synchronization of motor responses to visual stimuli during walking is goal-directed, alluding to a process of error minimization wherein proprioceptive and vestibular cues become more consistent with perceived mediolateral motion. However, while pseudorandom optical flow perturbations can elicit visuomotor entrainment, they are poorly equipped to provide mechanistic insight into its origin.

Error-augmentation is a paradigm in which movement errors are measured and augmented from an intended trajectory with the goal of strengthening movement control. Although not yet explicitly applied to the visuomotor control of head and trunk motion in walking, the paradigm has a rich history in the sensorimotor control literature, particularly in arm reaching tasks. Largely pioneered by Patton and colleagues, augmenting (i.e., increasing) sensory errors has been shown to effectively elicit motor adaptation while providing mechanistic insight into the origins of that adaptation. Regarding the role of vision in governing lateral balance in walking, there is a presumption that an overriding task goal in which spatial differences between actual motion of the head and trunk and sensory cues via optical flow are minimized. With error-augmentation, those visual errors can be systematically manipulated in real-time to understand their role in governing head and trunk position and thus stabilization during walking. Moreover, given its effect on motor learning and adaptation in arm reaching tasks, error-augmentation—here in the context of optical flow—may also recalibrate head and trunk control in walking toward the presence of after-effects following prolonged exposure.

Therefore, the purpose of this study was to investigate the role of visual errors in governing the sensorimotor control of head and trunk position during human walking as a means to explain the acute postural response to optical flow perturbations. A closed-loop visuomotor error augmentation task in an immersive virtual environment is used to introduce errors between the visual perception of self-motion and actual instantaneous motion of the head and trunk. The primary hypothesis that minimization of visual errors was tested, achievable during this task only by way of reduced lateral head and trunk movement, is an important and spontaneous feature governing the visuomotor control of human locomotion. The alternative hypothesis would be that visual feedback overrides other sensory modalities and is itself an independent control parameter in governing head and trunk position. To test this alternative hypothesis, the experimental paradigm was designed to include both positive (i.e., visual perception that amplified instantaneous head and trunk motion) and negative (i.e., visual perception that counteracted instantaneous head and trunk motion) visual feedback gains.

2. MATERIALS AND METHODS

2.1. Subjects

Twelve (12) subjects were recruited in this study (8 males, 4 females, age: 24.1±4.7 yrs., body mass: 73.3±13.0 kg; height: 176±9 cm, mean±standard deviation, S.D.). All subjects were healthy without any current neuromusculoskeletal disorders or injuries. Each subject provided written informed consent according to the approved protocol with the Biomedical Sciences Institutional Review Board of the University of North Carolina at Chapel Hill.

2.1.1. Experimental Protocol and Data Collection

A photocell timing system (Brower Timing Systems, Draper, UT) was first used to measure subjects' preferred overground walking speed (PWS) from the average of three durations taken to traverse the middle 2 m of a 10 m walkway at their normal, comfortable walking speed ($1.36\pm0.14$ m·s$^{-1}$). The subjects' PWS was established using an overground walking paradigm, which may yield a different speed than that using a treadmill walking paradigm. All subjects then walked at their PWS on an instrumented split-belt treadmill (1.45 m long×0.60 m wide belts, Bertec Corp., Columbus, Ohio). For all treadmill walking trials, subjects watched a speed-matched, immersive virtual hallway rear-projected onto a semi-circular screen (1.45 m radius×2.54 m height, see projection screen 102 in FIG. 1) surrounding the treadmill 104. Thirty (30) retroreflective markers were placed, including those on anatomical landmarks and marker clusters, on the 7th cervical vertebra (C7), pelvis, and right and left foot, shank, and thigh of the subject 106. Alternatively, the anatomical landmark may include to general areas of anatomical portions of the subject, such as a global head position of the subject and/or a global trunk position of the subject.

A 3D motion capture system (Motion Analysis Corp., Santa Rosa, Calif., 10 cameras) recorded the trajectories of each marker at 100 Hz. The mediolateral position of the C7 marker was chosen for the feedback control loop of the virtual hallway because C7 is the highest point on the body with large translation while not affected by head orientation. In some embodiments, the mediolateral displacement measurement is based on a difference of a mediolateral position of the dynamic virtual environment and an mediolateral position marker corresponding to specific anatomical points, such as the C7 vertebrae of the subject, or to general areas such as a global head position of the subject and/or a global trunk position of the subject. For example, the 3D motion capture system can be configured to capture image data of the global head position and/or global trunk position of the subject that can be used as the position data of the anatomical portion of the subject.

Mediolateral optical flow in the virtual environment was augmented in real-time based on instantaneous measurements of subjects' trunk position as follows. The mediolateral position of the C7 marker was streamed from the motion capture system through local Ethernet to another computer and received using a Simulink® real-time controller. The midline of the virtual hallway was set for all subjects as the middle of the treadmill, with mediolateral variations prescribed to match the C7 marker trajectory. Specifically, the end of the hallway always remained relatively stationary, while the foreground (e.g., foreground mediolateral position) moved according to this feedback paradigm, thereby emulating the subject's head and trunk position changes from one step to the next rather than heading corrections. In some trials, the mediolateral position of the virtual hallway was augmented by a factor (G) times the instantaneous mediolateral C7 position, thereby introducing an error between the visual perception of self-motion and the actual motion of the head and trunk of the subject 106. The factor G is thereby considered the gain defining the visual error magnitude which, in different trials, took four values (i.e., ±2.5, ±5.0). The 5.0 magnitude gain was determined in pilot testing to be the largest possible while ensuring that the virtual hallway remained on the projection screen. Positive/negative gains indicate virtual hallway mediolateral motion was in the same/opposite direction of the instantaneous mediolateral C7 motion, respectively. The feedback delay between the C7 marker position and resulting changes to virtual hallway measured ~14 milliseconds using the available Software Development Toolkit (Motion Analysis Corp.). Subjects were verbally instructed to only "walk on the treadmill while watching the hallway" to record naturally emergent patterns in response to error-augmented optical flow.

Subjects first completed one 3-minute trial at their PWS with zero gain ("Baseline"). Subjects then completed four 11-minute walking trials in fully randomized order that incorporated error-augmented optical flow (i.e., "adaptation"). As shown in diagram 110 in FIG. 1, each of those walking trials consisted of 10 minutes in the presence of an error augmentation gain on optical flow followed by 1 min of walking with zero gain (i.e., "Post-adaptation"). At the beginning of each 11-min trial, subjects walked for 15 seconds with a fixed optical flow to reach a steady state walking pattern on the treadmill 104.

2.1.2. Data Analysis

The C7 marker was used as a surrogate for the trunk motion that is insensitive to the head turns. The C7 marker's trajectories were filtered using a 4th-order zero-lag low-pass digital Butterworth filter with a cutoff frequency of 8 Hz. Dependent variables for head and trunk position included the step-to-step range of mediolateral trunk motion (intra-step measure, see FIG. 4), and the root means square (RMS) of mediolateral trunk position (inter-step measure, see FIG. 5). The time series of step length and step width were also calculated to resolve step-to-step adjustments in foot placement. Specifically, step lengths were calculated as the relative anterior-posterior position of consecutive heel markers at heel strike plus the treadmill belt translation during that step. Step widths were calculated as the mediolateral distance between consecutive heel positions at heel strike. From their time series, mean step length and step width and their respective variabilities were calculated—the latter reported as the standard deviation as shown in Tables 1 and 2 below. Notably, Table 1 (positive feedback gains) and Table 2 (negative feedback gains) show the effects of error-augmented optical flow on foot placement kinematics (cm).

TABLE 1

| | | Positive feedback gains ($G^+$) | |
| --- | --- | --- | --- |
| | | 5.0 | 2.5 |
| SW (14.8 ± 3.8) | Early | 15.0 ± 5.2 | 15.1 ± 5.6 |
| | Middle | 14.6 ± 4.6 | 14.0 ± 4.5 |
| | Late | 14.6 ± 5.3 | 14.5 ± 5.8 |
| | post | 12.1 ± 3.9* | 13.1 ± 4.7* |
| SW (70.5 ± 6.3) | Early | 70.3 ± 7.1 | 70.3 ± 6.8 |
| | Middle | 70.6 ± 7.2 | 71.0 ± 6.7 |
| | Late | 70.7 ± 7.1 | 71.4 ± 6.5 |
| | post | 71.6 ± 6.9* | 71.8 ± 6.9* |
| SW (2.3 ± 0.6) | Early | 2.7 ± 0.7 | 2.5 ± 0.5 |
| | Middle | 2.9 ± 0.9* | 2.7 ± 0.6* |
| | Late | 3.0 ± 0.9* | 2.8 ± 1.1* |
| | post | 2.6 ± 0.7 | 2.5 ± 0.7 |
| SW (2.1 ± 0.6) | Early | 2.2 ± 0.7 | 2.1 ± 0.7 |
| | Middle | 2.1 ± 0.4 | 1.8 ± 0.5 |
| | Late | 2.1 ± 0.6 | 2.1 ± 1.0 |
| | post | 1.9 ± 0.5 | 1.9 ± 0.7 |

TABLE 2

| | | Negative feedback gains ($G^-$) | |
| --- | --- | --- | --- |
| | | 5.0 | 2.5 |
| SW (14.8 ± 3.8) | Early | 15.3 ± 5.0 | 15.3 ± 5.2 |
| | Middle | 13.7 ± 4.5 | 13.7 ± 4.2 |
| | Late | 14.1 ± 4.9 | 13.9 ± 4.5 |
| | post | 15.4 ± 4.9 | 14.5 ± 5.1 |
| SW (70.5 ± 6.3) | Early | 70.1 ± 6.8 | 69.5 ± 5.7 |
| | Middle | 71.0 ± 6.7 | 70.9 ± 6.6 |
| | Late | 70.9 ± 6.7 | 71.1 ± 6.8 |
| | post | 70.3 ± 6.7 | 70.8 ± 6.8 |
| SW (2.3 ± 0.6) | Early | 2.9 ± 0.9 | 2.5 ± 0.6 |
| | Middle | 2.9 ± 0.8* | 2.5 ± 0.9 |
| | Late | 3.0 ± 0.8* | 2.7 ± 0.9 |
| | post | 2.4 ± 0.6 | 2.5 ± 0.9 |
| SW (2.1 ± 0.6) | Early | 2.2 ± 0.5 | 2.1 ± 0.7 |
| | Middle | 2.0 ± 0.5 | 1.9 ± 0.6 |
| | Late | 1.9 ± 0.5 | 2.0 ± 0.6 |
| | post | 2.0 ± 0.6 | 1.9 ± 0.7 |

As indicated above, Tables 1 and 2 illustrate the effects of error augmented optical flow on foot placement kinematics (cm). The data represented in Tables 1 and 2 are mean±standard deviation. Notations represented in Tables 1 and 2 are as follows: SW: step width, SL: step length, SWV: step width variability, SLV: step length variability. Baseline values from normal walking are shown in parentheses. Asterisks (*) indicate significantly different ($p<0.05$) from baseline walking.

2.2. Statistical Analysis

First, pairwise t-tests were used to compare dependent variables from the last minute of the 3-min baseline walking trial to those extracted from walking with error-augmented optical flow (min 1 ["Early"], min 5 ["Middle"], min 10 ["Late"] in adaptation), including after-effects from so. For any pairwise comparison in the texts, effect size is reported as Cohen's d. Second, two, 2-way repeated measure ANOVAs were utilized to determine the effects of and interactions between Magnitude (i.e., 2.5, 5.0) and Phase (i.e., min 1—"Early", min 5—"Middle", and min 10—"Late") for error-augmented optical flow with: (i) positive and (ii) negative feedback gains including the effect size ($\eta^2$). When a significant main effect or interaction was found, post-hoc pairwise comparisons were performed to identify which conditions produced those effects. A Bonferroni correction adjusted the level of significant main effect for post-hoc pairwise comparisons with a critical alpha level of 0.0085. In addition, the three tests conducted within each 2-way repeated measure ANOVA may cause alpha inflation. This problem was mitigated using two procedures: (i) the sequential Bonferroni (seqB) correction procedure was used to control the familywise error rate (FWER) by evaluating each null hypothesis against an level adjusted to control for the inflated probability of a Type I error; (ii) the Benjamini-Hochberg (BH) procedure was used to control the false discovery rate (FDR, Type II error). All statistics were coded in MATLAB (MathWorks Inc., Natick, Mass.). The results of these procedures are summarized in Appendix Tables A and B (see below).

3. RESULTS 3.1. The Effects of Error-Augmented Optical Flow on Trunk Motion

Figure 2:
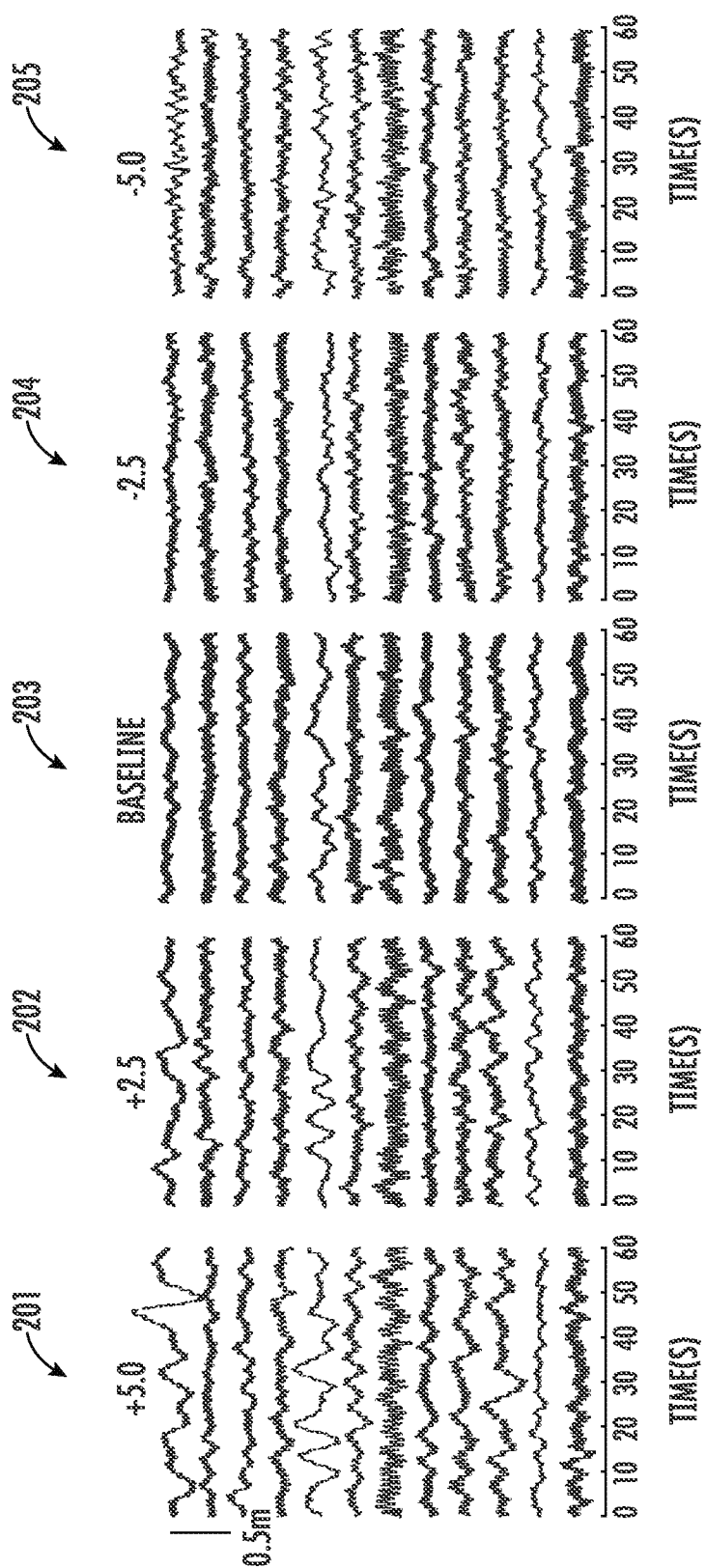
FIG. 2 illustrates a plurality of graphs exhibiting the mediolateral trunk motion of individual subjects in response to various error-augmented optical flows according to an embodiment of the subject matter described herein.
Figure 3:
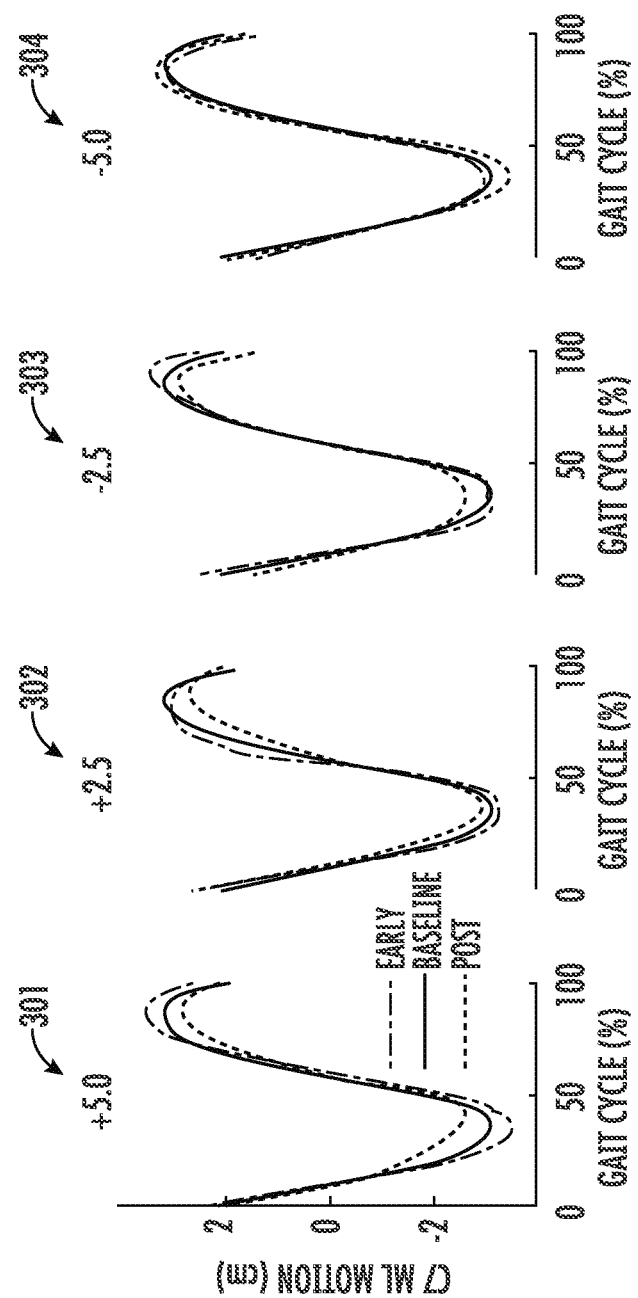
FIG. 3 illustrates a plurality of graphs exhibiting stride-averaged mediolateral seventh cervical vertebrae positions associated with various error augmented optical flows according to an embodiment of the subject matter described herein.

Mediolateral trunk motion from individual subjects during their initial response to error-augmented optical flow compared to baseline walking is summarized in FIG. 2, with stride-average profiles shown in FIG. 3. FIG. 3 illustrates a plurality of graphs 301-304 exhibiting stride-averaged mediolateral C7 vertebrae positions associated with various error augmented optical flows according to an embodiment of the subject matter described herein. Notably, stride-averaged mediolateral (ML) C7 position during baseline walking (solid gray line) compared to early exposure (black solid line) and after-effects following cessation of error-augmented optical flow (gray dotted line, i.e., post) for visual gains of G=+5.0 (as shown in graph 301), G=+2.5 (as shown in graph 302), G=−2.5 (as shown in graph 303), and G=−5.0 (as shown in graph 304). Each curve was first averaged across all steps taken in that respective phase and then averaged across all subjects. Zero on the ordinate refers to the midline of the treadmill.

Figure 4:
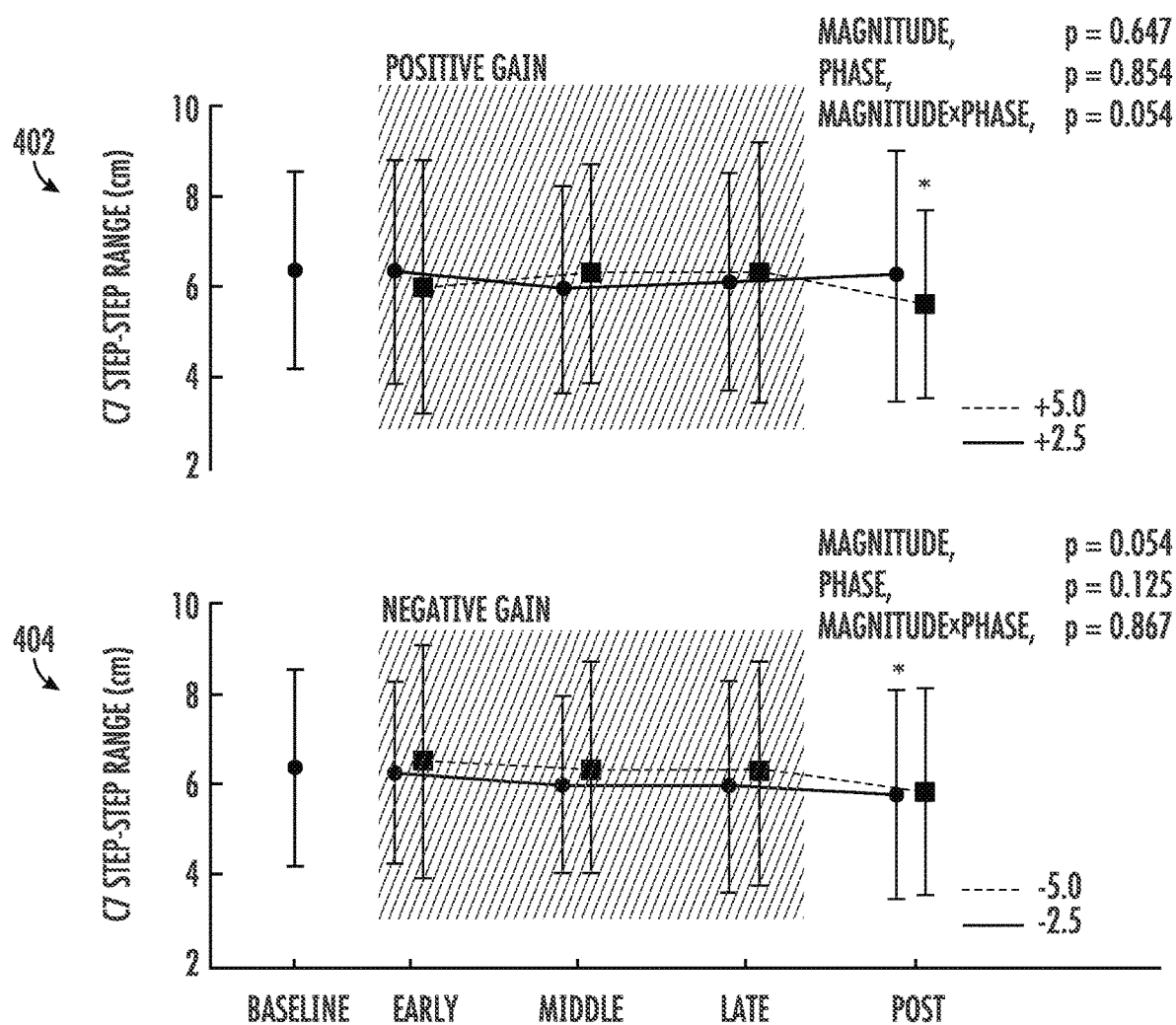
FIG. 4 illustrates graphs exhibiting intra-step outcome measurements that quantify head and trunk motion during walking according to an embodiment of the subject matter described herein.

FIG. 4 illustrates graphs exhibiting intra-step outcome measurements that quantify head and trunk motion during walking according to an embodiment of the subject matter described herein. Notably, this figure illustrates the intra-step outcome measurement that quantifies a subject's head and trunk motion during walking. FIG. 4 shows the group average (standard deviation) range of step-to-step mediolateral trunk position at different phases (early, middle, and late) of exposure to error-augmented optical flow with (A) positive (see graph 402) and (B) negative (see graph 404) visual gains compared to baseline walking and after-effects following cessation (post). Asterisks (*) indicate significant (p<0.05) difference compared to baseline walking. The main effects and interaction terms from the repeated measures ANOVA during exposure are included. The corresponding F values and effect sizes ($\eta^2$) for these statistical comparisons follow: $F_{mag}(1,11)=0.22$, $\eta_{mag}^2=0.02$; $F_{phase}(2,22)=0.16$, $\eta_{phase}^2=0.01$; $F_{mag*phase}(2,22)=3.34$, $\eta_{mag*phase}^2=0.23$ in panel A. $F_{mag}(1,11)=4.64$, $\eta_{mag}^2=0.30$; $F_{phase}(2,22)=2.29$, $\eta_{phase}^2=0.17$; $F_{mag*phase}(2,22)=0.14$, $\eta_{mag*phase}^2=0.01$ in panel B.

Figure 5:
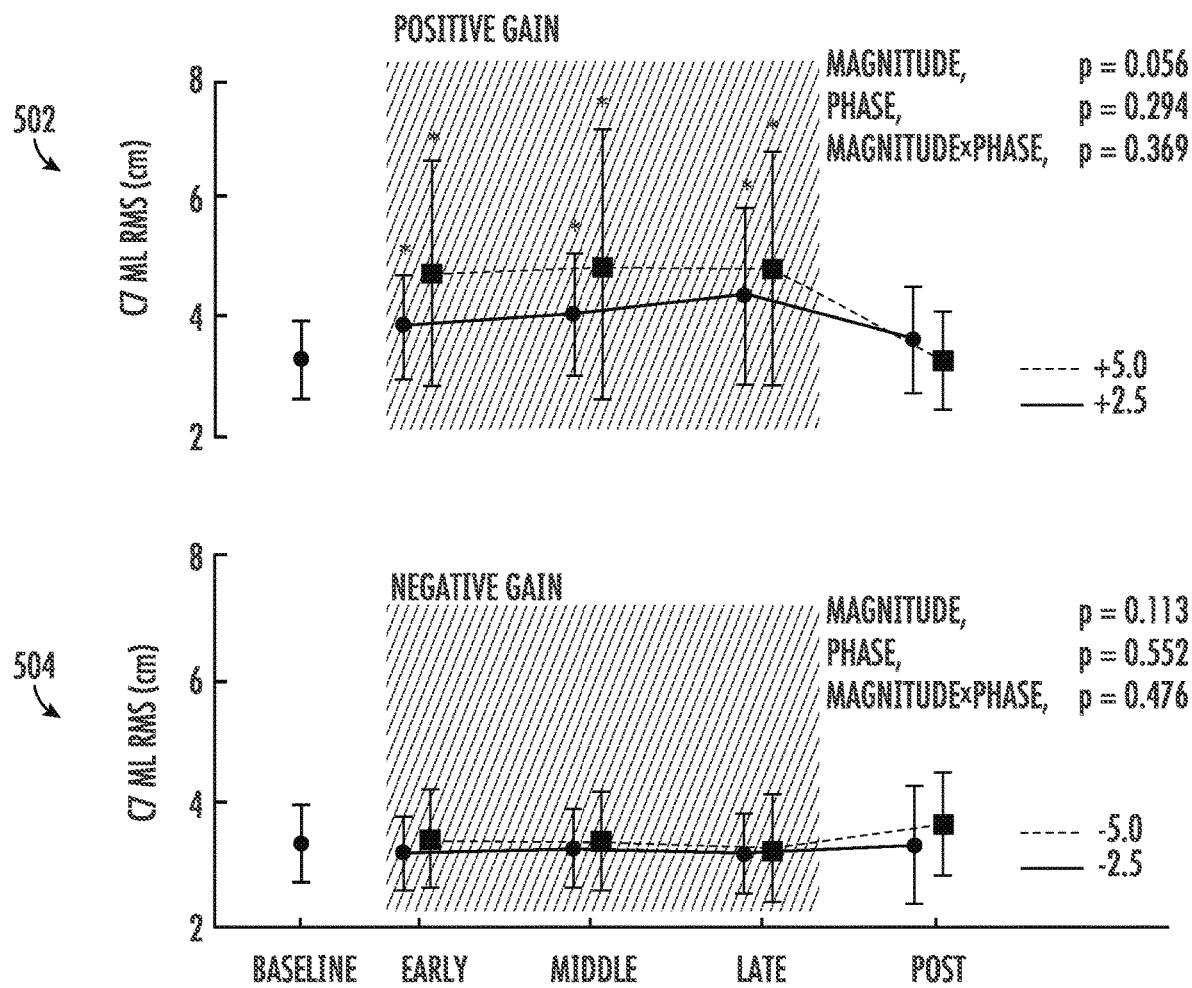
FIG. 5 illustrates graphs exhibiting inter-step outcome measurements that quantify head and trunk motion during walking according to an embodiment of the subject matter described herein.

Similarly, FIG. 5 illustrates graphs exhibiting inter-step outcome measurements that quantify head and trunk motion during walking according to an embodiment of the subject matter described herein. Notably, this figure illustrates the inter-step outcome measurement that quantifies a subject's head and trunk motion during walking. The figure shows the group average (standard deviation) root mean square (RMS) of mediolateral (ML) trunk position at different phase (early, middle, and late) of exposure to error-augmented optical flow with (A) positive and (B) negative visual gains compared to baseline walking and after-effects following cessation (post). Asterisks (*) indicate significant (p<0.05) difference compared to the baseline. The main effects and interaction terms from the repeated measures ANOVA during exposure are included. The corresponding F values and effect sizes ($\eta$2) for these statistical comparisons follow: $F_{mag}(1,11)=4.56$, $\eta_{mag}^2=0.29$; $F_{phase}(2,22)=1.29$, $\eta_{phase}^2=0.11$; $F_{mag*phase}(2,22)=1.04$, $\eta_{mag*phase}^2=0.09$ in panel A. $F_{mag}(1,11)=2.97$, $\eta_{mag}^2=0.21$; $F_{phase}(2,22)=0.61$, $\eta_{phase}^2=0.05$; $F_{mag*phase}(2,22)=0.77$, $\eta_{mag*phase}^2=0.07$ in panel B.

Neither intra- (p-values>0.066, see FIG. 4) nor inter-step (p-values>0.162, see FIG. 5) measures of mediolateral trunk motion magnitude decreased in the presence of error-augmented optical flow. Rather, compared to baseline, positive visual errors increased the RMS of mediolateral trunk position (early vs. baseline; G=+2.5: F(1, 11)=10.27, p=0.008, Cohen's d=0.73, G=+5.0: F(1, 11)=7.90, p=0.017, d=1.02, graph 502 in FIG. 5). Moreover, this effect on the inter-step measure of trunk motion scaled in proportion to feedback gain magnitude (main effect, p=0.056). The intra-step measure, step-to-step mediolateral trunk range of motion magnitude, was unaffected by the presence of error-augmented optical flow with positive gains (early vs. baseline; G=+2.5: F(1, 11)=0.07, p=0.803, d=−0.03, G=+5.0: F(1, 11)=1.05, p=0.327, d=−0.15, see graph 402 in FIG. 4). These early responses to error-augmented optical flow with positive feedback gains were relatively stable; no significant phase effects were found on step-to-step mediolateral trunk range of motion (F(2, 22)=0.16, p=0.854, $\eta^2$=0.01, see graph 402 in FIG. 4) nor the RMS of mediolateral trunk position (F(2, 22)=1.29, p=0.294, $\eta^2$=0.11, see graph 502 in FIG. 5).

Compared to baseline, negative visual errors had no effect on intra-step (early vs. baseline; G=−2.5: F(1, 11)=0.32, p=0.586, Cohen's d=−0.07, G=−5.0: F(1, 11)=0.15, p=0.704, d=0.05, see graph 404 in FIG. 4) nor inter-step (see graph 504 in FIG. 5, early vs. baseline, F(1, 11)=0.77, p=0.399, d=−0.23, G=−2.5, F(1, 11)=0.49, p=0.500, d=0.13, G=−5.0) measure of mediolateral trunk motion. In addition, no main effect of time (i.e., phase) were found on either outcome measure (p-values>0.125, see graph 404 in FIG. 4 and graph 504 in FIG. 5).

Following the 'release' of error-augmented optical flow with positive feedback gains, the RMS of mediolateral trunk motion returned to baseline values within one minute (see graph 502 in FIG. 5). However, despite no apparent phase effects during exposure, step-to-step mediolateral trunk range of motion, the intra-step measure, decreased significantly in Post compared to baseline walking (−12% for G=+5.0, F(1, 11)=17.72, p=0.002, d=−0.35, see graph 402 in FIG. 4; −10% for G=−2.5, F(1, 11)=5.57, p=0.038, d=−0.28, see graph 404 in FIG. 4).

3.2. The Effects of Error-Augmented Optical Flow on Foot Placement Kinematics

Compared to baseline, no significant immediate effect of error-augmented optical flow were found on step length, step width, nor their variabilities (early vs. baseline, p-values>0.063, Table 1). Significant effect of gain magnitude on foot placement kinematics (p-values 0.056, Table 1) were also not found. In contrast, time-dependent changes were found during prolonged exposure due to an error-augmented optical flow that was more pronounced for negative than positive visual errors. Specifically, step width (F(2,22)=15.3, $p_{phase}$=0.002, $\eta^2$=0.58) and step length variability (F(2, 22)=8.42, $p_{phase}$=0.014, $\eta^2$=0.43) decreased significantly with exposure to negative but not positive gains (Table 1). In contrast, step length increased for both positive (F(2, 22)=5.37, $p_{phase}$=0.041, $\eta^2$=0.33) and negative (F(2, 22)=27.11, $p_{phase}$<0.001, $\eta^2$=0.71) gains during exposure. Finally, following "release" of error-augmented optical flow, after-effects in trunk motion were accompanied by significantly longer (F(1, 11)=7.07, p=0.02, d=0.17) and narrower (F(1, 11)=25.08, p<0.001, d=−0.71) steps than baseline, but only following walking with positive gains (Table 1).

4. DISCUSSION

The primary outcome of this study is that humans appear not to spontaneously minimize visual errors, or those between the visual perception of movement and actual movement of the trunk, during walking. The results are instead more consistent with the alternative hypothesis—that visual feedback can override other sensory modalities and independently compel adjustments in head and trunk position. Little evidence was also found that head and trunk kinematics exhibit time-dependent adaptation during prolonged exposure to error-augmented optical flow in young adults. However, aftereffects do allude to a recalibration of head and trunk stabilization toward more tightly regulated postural control following prolonged exposure to error-augmented optical flow.

4.1. Effects of Error-Augmented Optical Flow: Exposure Versus Normal Walking The effects of error-augmented optical flow differed fundamentally from those due to pseudorandom optical flow perturbations, which are more commonly used in the study of balance in walking. For example, compared to normal, unperturbed walking, optical flow perturbations can elicit two- to four-fold increases in foot placement variability and completely decorrelate the step-to-step structure of step width. In contrast, error-augmented optical flow elicited only subtle changes in foot placement variability. This suggests that lateral balance control in walking is uniquely susceptible to perturbations designed to enhance the visual perception of lateral instability, and not merely to generalized errors in the visual perception of self-motion. Nevertheless, visuomotor control in walking is inherently closed-loop, and error-augmented optical flow affected that control during exposure in ways that inform the broader understanding of walking balance and response to perturbations.

The young adults in the study were unable to, or at least did not, maintain their mediolateral trunk motion near the middle of the treadmill walking surface following exposure to error-augmented optical flow. The optical flow paradigm used the treadmill's midline as a reference for prescribing visual errors. Specifically, the visual perception of mediolateral motion is augmented as subjects deviated from the treadmill midline, first due to mediolateral trunk oscillations and then further due to changes in average trunk position. Accordingly, in response to positive feedback gains that would act to "push" them away from the treadmill midline, most individual subject trunk trajectories showed low-frequency drift, each corrected throughout several steps, which was not apparent during normal walking as shown in FIG. 2. FIG. 2 illustrates a plurality of graphs 201-205 exhibiting the mediolateral trunk motion of individual subjects in response to various error-augmented optical flows and the baseline optical flow according to an embodiment of the subject matter described herein. Specifically, the graphs illustrate the medio-lateral position of the trunk (C7 marker) during early exposure for visual gains of G=+5.0 (as shown in graph 201), G=+2.5 gain (as shown in graph 202), G=−2.5 (as shown in graph 204), and G=−5.0 (as shown in graph 205) compared to baseline walking (G=0) (as shown in graph 203) for each subject.

The "corrections" toward the treadmill midline may be explained by subjects realizing and responding to the physical bounds set by the width of the walking surface. Ultimately, those dynamics likely underlie the increased RMS of mediolateral trunk motion measured in response to positive feedback gains.

There are other possible explanations why error-augmented optical flow with positive gains, but not negative gains, increased the excursion (i.e., RMS) of mediolateral trunk position. During walking, humans can distinguish the direction to which they are walking (i.e., their heading) from the direction at which they are looking (e.g., a fixed object in their environment). When walking down a hallway, humans may rely on the fixed position of walls in their periphery as an anchored reference for head and trunk stabilization. In the presence of positive visual errors, postural deviations to the right would move that anchored reference of the wall to the right by an amount proportional to feedback gain magnitude. In this example, only by continuing to move to the right would subjects preserve the same relative distance to the anchored reference. This behavior could form a positive feedback loop that would continue to "pull" the body toward the right sidewall of the virtual hallway, an influence that would be altogether absent in the presence of negative visual errors. Therefore, it is posited that an anchored visual reference, in one scenario the walls of the virtual hallway, provide additional spatial information for visuomotor control that is leveraged for head and trunk stabilization.

4.2. Effects of Error-Augmented Optical Flow: Prolonged Exposure and After-Effects Based on prior evidence that subjects adapt to pseudorandom optical flow perturbations, it is hypothesized that the outcome measures would exhibit tuning via time-dependent changes with prolonged exposure. The data did not fully support this hypothesis. Subjects' behavioral response to error-augmented optical flow was relatively invariant across the duration of each trial. Some evidence suggests that humans adapt their step-to-step control of step width to regulate mediolateral motion of the trunk, measured here via the C7 marker. This may explain why time-dependent changes were observed in SWV along with relatively well-preserved trunk kinematics. Also, time-dependent effects on step width and step length variability, apparent in response to negative gains, were inconsistent across the two amplitudes. Compared to those following the onset of optical flow perturbations, initial effects were generally smaller in response to the present paradigm. In light of these smaller effects, one interpretation is that there was less need for or benefit to adapting to error augmented optical flow during each 10-min trial. However, it is suspected that some adaptation did occur; as hypothesized, prolonged exposure to error-augmented optical flow elicited aftereffects that persisted following "release" of error-augmented optical flow. Most notably, these aftereffects included longer, narrower steps, and smaller step-to-step mediolateral trunk range of motion, particularly following exposure to larger amplitude positive feedback gains. Here, the "release" of error-augmented optical flow is seen as analogous to catch trials in arm reaching paradigms that use error-augmentation. Specifically, the cessation of error-augmentation is generally designed to reveal changes in the underlying strategies used to control movement. Accordingly, the measured aftereffects in the study are interpreted to suggest that head and trunk stabilization had become more tightly regulated following exposure compared to baseline. Such an outcome would be anticipated if error-augmented optical flow with positive gains increased the demands placed on the postural control system, presumably to maintain head and trunk position near the midline of the treadmill with smaller mediolateral oscillations.

That subjects exhibited at least temporary reductions in step-to-step postural sway after exposure to error-augmented optical flow may have translational implications. Most falls occur during locomotor activities such as walking, during which preserving the body's center of mass within the mediolateral base of support is important for balance integrity. Accordingly, individuals with excessive mediolateral postural sway may be at a greater risk of lateral instability and falls. Some evidence suggests that visual feedback can facilitate improved motor learning with beneficial effects. However, it is unclear what type of optical flow paradigm is the best. Balance perturbations, for example via mediolateral optical flow oscillations, provide the opportunity to practice reactive adjustments with promising effects on balance control and reducing falls risk. Conversely, error-augmented optical flow with positive feedback gains may lead to more tightly regulated postural control following exposure. Because perturbations and error augmentation via optical flow represent fundamentally different paradigms for balance training, thereby differing in their elicited responses and aftereffects, specific recommendations for clinical translation are challenging. The advent and more widespread adoption of wearable and low-cost virtual reality technology should inspire continued research toward determining which optical flow paradigms, or combinations thereof, can provide the most beneficial effect on balance integrity, for example, in older adults or in patients with neurodegenerative diseases at high risk of falling.

4.3. Limitations

Foremost, the implications of the outcomes for balance control in people with walking balance deficits or those at risk of falls are discussed. This study focused on otherwise healthy young subjects. Accordingly, the results may not generalize to those populations in the way that was predicted. In addition, for practical considerations in the study's design, 10-min trials were opted for. The response to longer exposure to error-augmented optical flow, like what might be expected from a training paradigm, are difficult to anticipate. The C7 marker provides a surrogate representation of trunk translation. Future work may consider the complexities of head rotation together with trunk translation. Treadmill walking speed may also be constrained, and the response to error-augmented optical flow may have differed if subjects were allowed to regulate their walking speed throughout each trial like when navigating real-world environments. Finally, after-effects reported herein allude to changes in neuromuscular control that the experimental design was not equipped to fully capture. Future studies involving electromyographic recordings, particularly of postural control muscles, may provide important insight into those changes in control.

Figure 6:
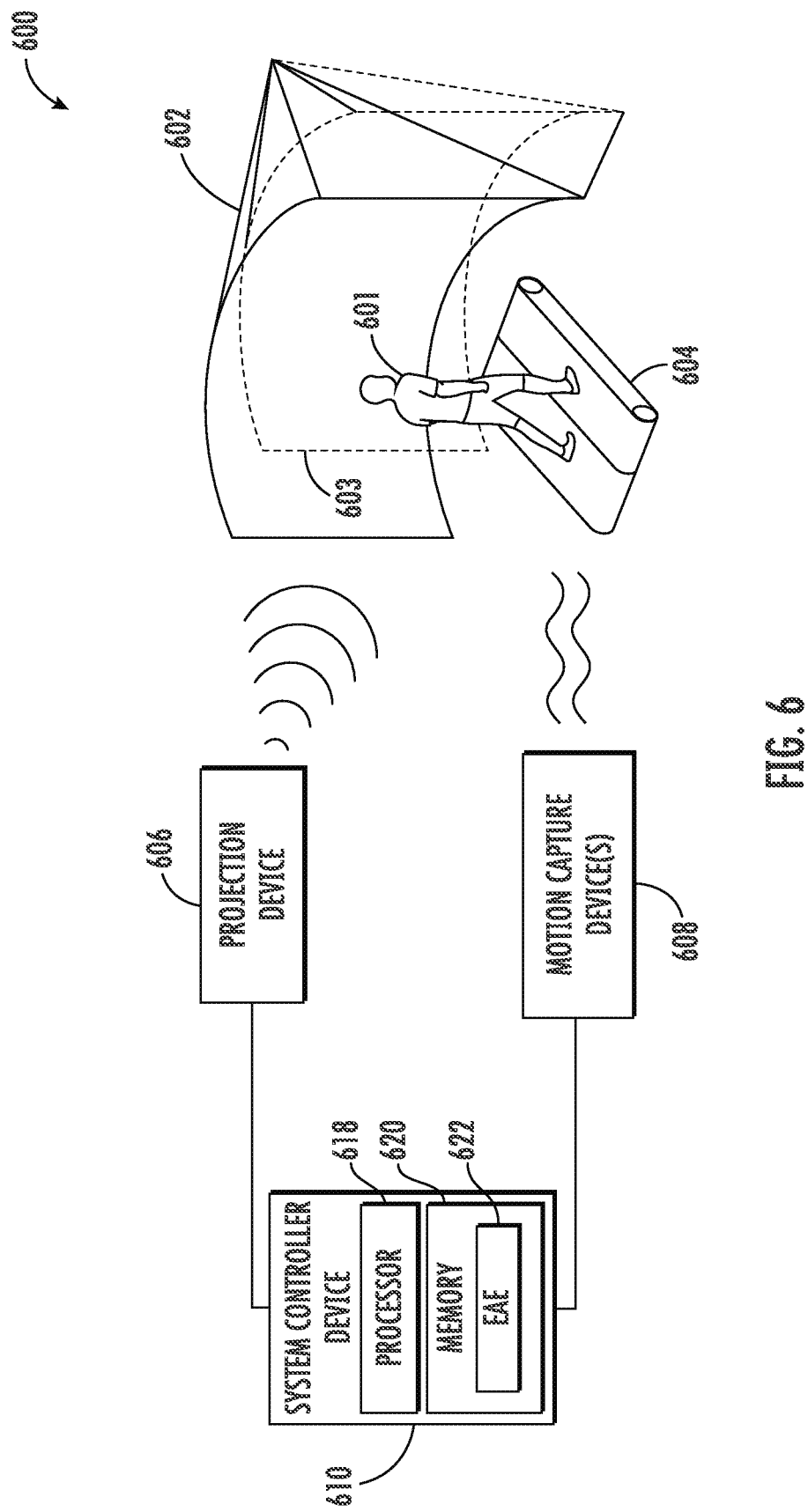
FIG. 6 illustrates a exemplary system diagram configured for utilizing visuomotor error augmentation for balance rehabilitation according to an embodiment of the subject matter described herein.

FIG. 6 illustrates an exemplary system diagram configured for utilizing visuomotor error augmentation for balance rehabilitation according to an embodiment of the subject matter described herein. For example, FIG. 6 depicts a human subject 601 walking on a treadmill device 604 while watching an immersive virtual hallway 603 (that is being projected by a projection device 606 on a projection screen 602) with the continuous optical flow while motion capture monitoring the instantaneous position of a $7^{th}$ cervical vertebrae (C7) marker associated with subject 601. While the following disclosure describes the optical flow as being a 'continuous optical flow', the disclosed subject matter may also utilize a non-continuous optical flow in some embodiments (e.g., embodiments in which the system elicits a one-off type of change that is not necessarily continuous as the subject is walking). This may resemble a single wave oscillation affecting a single step. Moreover, while the system is described herein as generalized to utilize a projection device and projection screen, embodiments that alternatively utilize a display device, such as a wearable virtual reality (VR) headset device or other similar portable devices are within the scope of the disclosed subject matter.

Using a motion capture device 608 (e.g., and a real-time system controller device 610, the mediolateral position of the projected virtual hallway 603 was captured and visually prescribed to match that instantaneous C7 position in the mediolateral direction. In some embodiments, motion capture device 608 includes a 3D motion capture system (Motion Analysis Corp., Santa Rosa, Calif., 10 cameras) configured to record the trajectories of the subject's mediolateral positional markers at 100 Hz and the controller device 610 includes a Simulink® real-time controller configured to receive a stream of the mediolateral position of the C7 marker from the motion capture device 608 via local Ethernet. In some embodiments, a position sensor device can be used instead of motion capture device 608 and can comprise a system including on-board inertial measurement units or devices. System controller device 610 may include one or more processors 618, such as a central processing unit (e.g., a single core or multiple processing cores), a microprocessor, a microcontroller, a network processor, an application-specific integrated circuit (ASIC), or the like. System controller device 610 may also include memory 620. Memory 620 may comprise random access memory (RAM), flash memory, a magnetic disk storage drive, and the like. In some embodiments, memory 620 may be configured to store an error augmentation engine 622, which can be executed by processor(s) 618.

In some trials, visual errors were introduced by augmenting the mediolateral virtual hallway position by a factor, G, defined as the visual gain between the visual perception of the subject's trunk motion and the actual motion of the subject's trunk, which took values of ±2.5 and ±5.0. Subjects first completed one 3-minute trial at their PWS with zero gain ("Baseline," G=0). For each of the four previously mentioned gains, the experimental protocol started with zero gain of 15 seconds to acclimate treadmill walking at zero gain (i.e., normal optical flow, G=0) and followed by 10 min of exposure (i.e., adaptation) to error-augmented optical flow and finally by 1 minute after cessation of error-augmented optical flow (G=0). Outcome measures were extracted from the first ("early"), fifth ("middle"), and tenth ("late") minute of walking with the error-augmented optical flow for analysis.

Figure 7:
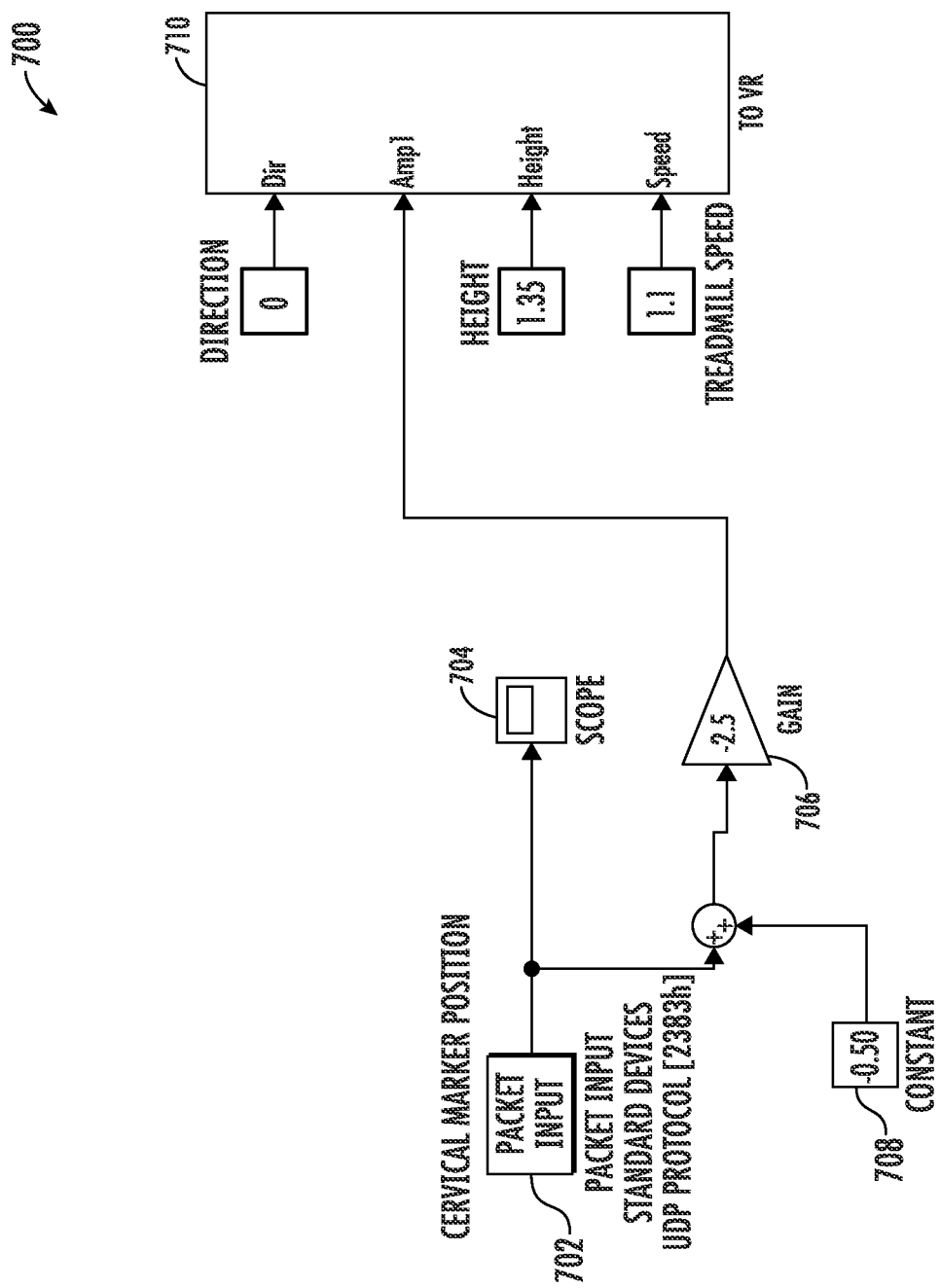
FIG. 7 illustrates a block diagram of the primary level of an exemplary real-time controller configured to utilize visuomotor error augmentation for balance rehabilitation according to an embodiment of the subject matter described herein.

FIG. 7 illustrates a block diagram of a primary of an exemplary real-time controller (e.g., system controller device 610 shown in FIG. 6) configured to utilize visuomotor error augmentation for balance rehabilitation according to an embodiment of the subject matter described herein. For example, FIG. 7 depicts a data packet input 702 (i.e., C7 marker's position) from a motion capture device, which is on a separate computer (608), that provides a subject's C7 marker's position. The data packet input may be modified by a constant 708 for scaling, and subsequently provided to an amplifier 706. Amplifier 706 can be configured to amplify the input by applying a predefined gain, G (e.g., G=±2.5 or ±5.0). The amplified signal is then provided as one of four inputs into a second layer (represented as block 710) of the system controller device. Block 710 further receives a direction parameter, a subject's body height parameter, and a treadmill speed parameter as inputs.

Figure 8:
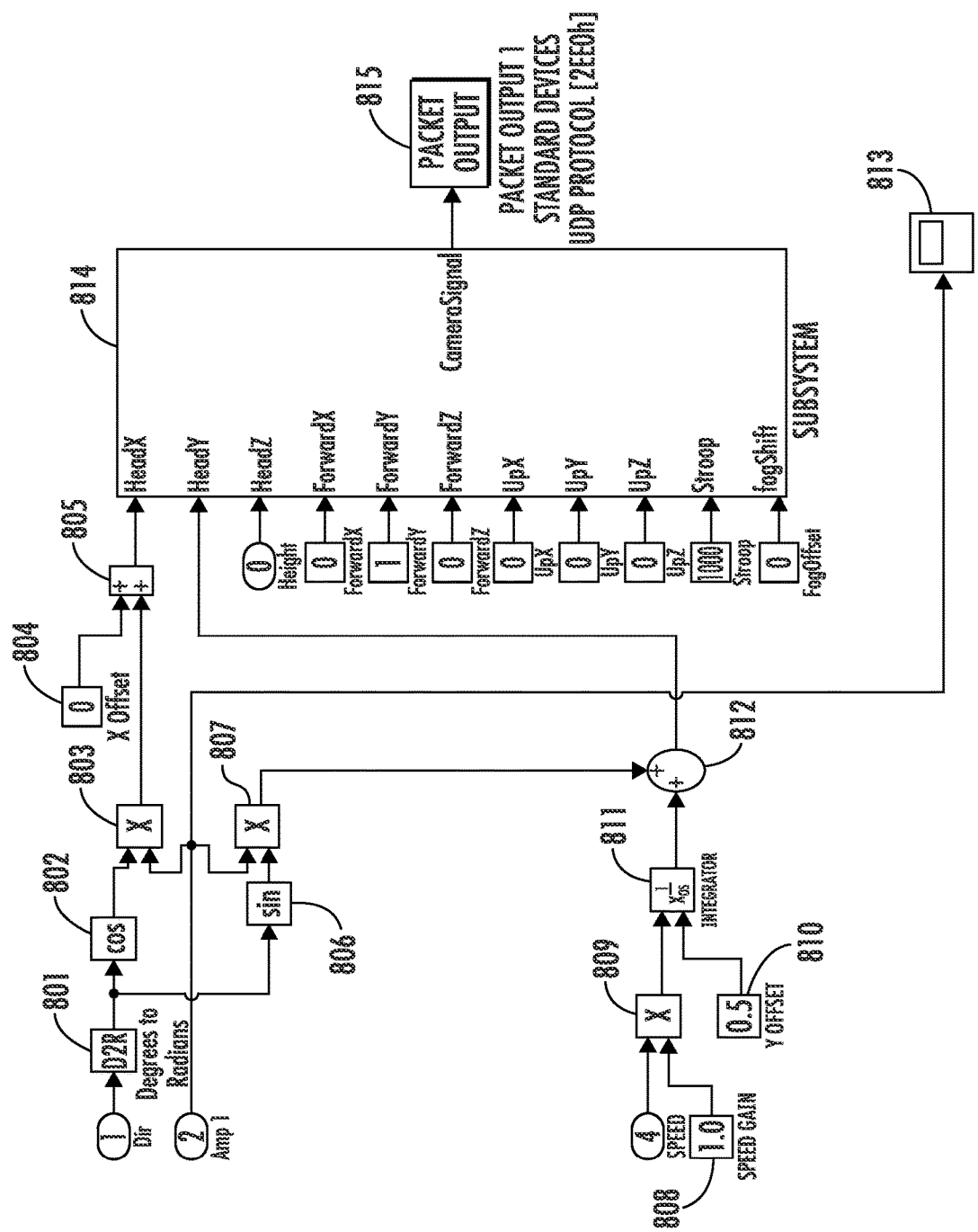
FIG. 8 illustrates a block diagram of the secondary level of an exemplary real-time controller configured to utilize visuomotor error augmentation for balance rehabilitation according to an embodiment of the subject matter described herein.

FIG. 8 illustrates a block diagram of the secondary level of an exemplary real-time controller configured to utilize visuomotor error augmentation for balance rehabilitation according to an embodiment of the subject matter described herein. In FIG. 8, the augmented error of the position of the C7 marker is amp1. Amp 1 is then fed to control the mediolateral position of the virtual hallway (i.e., HeadX). The Dir is an angle measured by degrees. The default value of Dir is zero, indicating Amp 1 (i.e., the augmented error of the position of the C7 marker) applies in the mediolateral direction (i.e., HeadX). If the value of Dir is changed to 90 degrees, it means that the Amp 1 is applied in the anterior-posterior direction (i.e., HeadY) of the virtual hallway. Specifically, component 801 converts the Dir from degrees to radians; components 802 and 806 project the Amp 1 into the mediolateral (i.e., HeadX) and anterior-posterior (i.e., HeadY) directions, respectively. Component 808 is the speed of the treadmill, which is a constant determined from user input. The speed of the treadmill is integrated with respect to time by component 811 to determine the position of the avatar along the anterior-posterior direction (i.e. HeadY).

Figure 9:
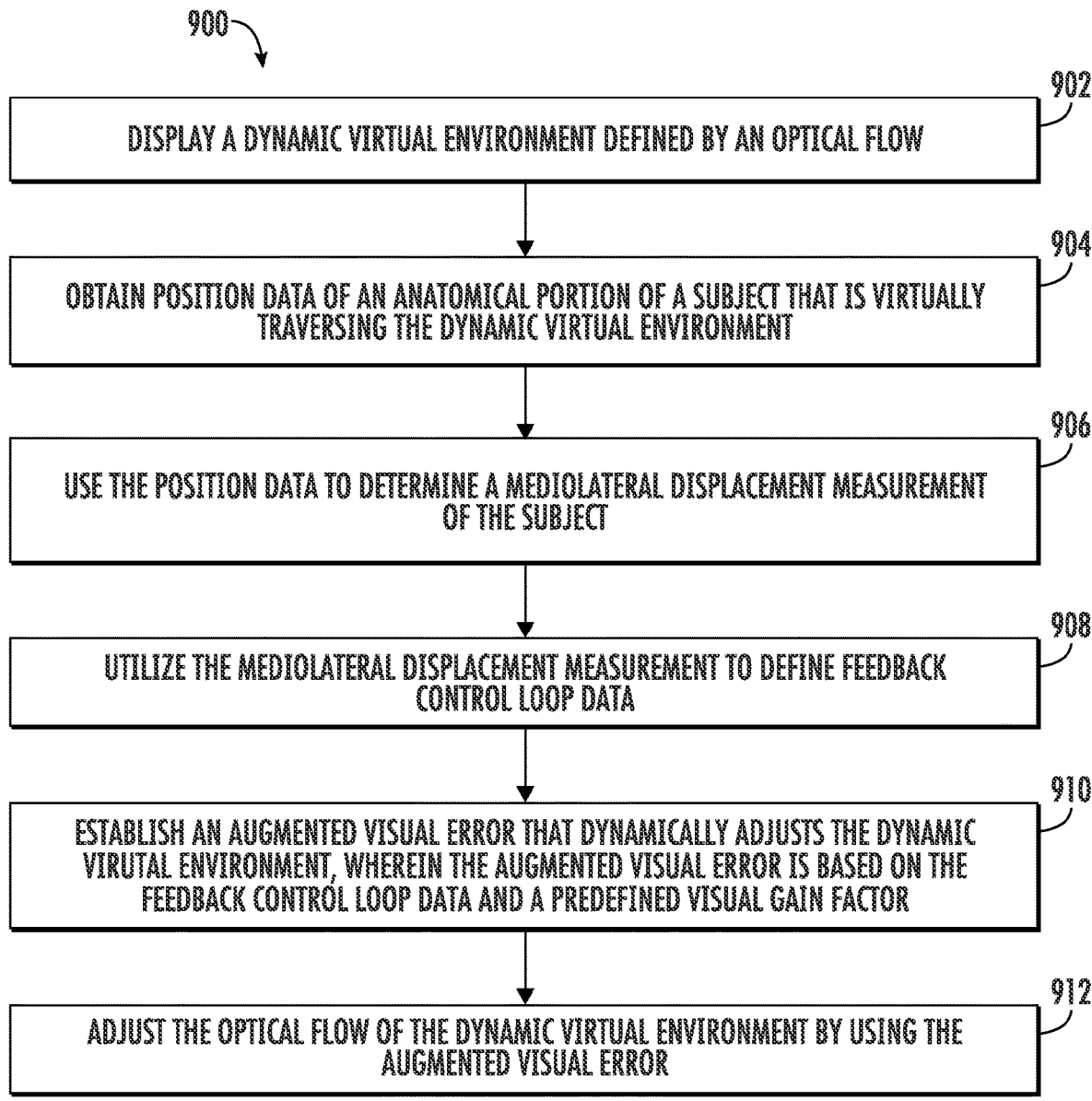
FIG. 9 illustrates a flow chart of a method for utilizing visuomotor error augmentation for balance rehabilitation according to an embodiment of the subject matter described herein.

FIG. 9 illustrates a flow chart of a method 900 for utilizing visuomotor error augmentation for balance rehabilitation. In some embodiments, method 900 includes an algorithm that can be stored in memory and executed by a processor. In step 902, a dynamic virtual environment defined by an optical flow is displayed (e.g., via projection or a display device, such as a wearable VR headset device). In some embodiments, the subject walked on a treadmill while viewing a virtual hallway that is characterized by continuous optical flow (or in some embodiments, a non-continuous optical flow). The dynamic virtual environment, such as the virtual hallway, is projected by one or more projection devices (or displayed in a wearable VR headset device or other portable display device).

In step 904, position data of an anatomical portion associated with a subject that is virtually traversing the dynamic virtual environment is obtained. In some embodiments, a motion capture device is configured to monitor the instantaneous position of the C7 vertebrae of the subject. For example, a mediolateral position marker may be placed on the subject on or near the C7 vertebrae. In other embodiments, the subject may wear a position sensor on the C7 vertebrae (or any other selected anatomical location). In some embodiments, the position data may include motion capture data obtained from a motion capture device or position sensor data obtained from a small inertial measurement unit (IMU).

In step 906, the position data is used to determine a mediolateral displacement measurement of the subject based on a difference of a mediolateral position of the dynamic virtual environment and a mediolateral position marker of the subject. In some embodiments, the motion capture device forwards the position data to a system controller device. The system controller device is then configured to utilize the position data to measure the distance (or differential) between the mediolateral position of the C7 marker and the mediolateral position of the projected virtual hallway.

In step 908, the mediolateral displacement measurement is utilized to define feedback control loop data. In some embodiments, the system controller device uses the difference between the medi0lateral position of the C7 marker and the mediolateral position of the projected virtual hallway as feedback control loop data. The feedback control loop data is provided as an adjustment signal to the display controller to adjust the mediolateral position of the displayed virtual hallway to increase the user's stabilization error.

In step 910, an augmented visual error that dynamically adjusts the dynamic virtual environment is established, wherein the augmented visual error is based on the feedback control loop data and a predefined visual gain factor. In some embodiments, the system controller device utilizes the feedback control loop data and a visual gain factor "G" as inputs to an algorithm that produces an augmented visual error. Notably, the augmented visual error can be used by the system controller device to dynamically adjust the dynamic virtual environment. In some embodiments, the augmented visual error constitutes an error between the visual perception of self-motion and the actual motion of the subject's head and trunk.

In step 912, the optical flow of the dynamic virtual environment is adjusted by using the determined augmented visual error. In some embodiments, the system controller device provides the augmented visual error as signal data to the projection device (or wearable VR headset device or other portable display device), which in turn adjusts the dynamic virtual environment by modifying the continuous optical flow (or non-continuous optical flow) that is perceived by the subject.

5. CONCLUSIONS

It is respectfully submitted that this is the first study to apply an error-augmentation paradigm to understand the role of visual errors in governing head and trunk stabilization during walking. In contrast to the earlier explanation for the mechanism governing visuomotor entrainment to optical flow perturbations, young subjects in the study did not respond consistently to minimize the errors between visual perception of movement and actual movement of the head and trunk. Thus, it cannot be concluded that unifying visual with vestibular and somatosensory feedback is always a universal control goal in human walking, at least in the context of head and trunk stabilization. Rather, visual feedback appears to override other sensory modalities and independently compel adjustments in head and trunk position. Finally, the results also have important translational implications. Although there was a focus on young adults, after-effects in the form of reduced mediolateral postural sway evident in the data may have important implications for the use of error-augmented optical flow to enhance the integrity of walking balance control through training, for example in older adults.

6. APPENDIX

Results from the sequential Bonferroni (seqB) and Benjamini-Hochberg (BH) procedures for the data included in Tables 1 and 2 above are presented below in Table A (for positive feedback gains) and Table B (for negative feedback gains).

In Tables A and B, the following notations are used: SW: step width, SL: step length, SWV: step width variability, SLV: step length variability. M: magnitude, P: Phase, M×P: the interaction between Magnitude and Phase. $\alpha_{adj}$seqB=the adjusted alpha level with the sequential Bonferroni procedure; $\alpha_{adj}$ BH=the adjusted alpha level with the Benjamini-Hochberg procedure; $H_0$ seqB=evaluation of the null hypotheses with the sequential Bonferroni procedure; $H_0$ BH=evaluation of the null hypotheses with the Benjamini-Hochberg procedure.

TABLE A

| | | Positive feedback gains (G⁺) | | | | |
|---|---|---|---|---|---|---|
| Effect | | p value | $\alpha_{adj}$SeqB | $\alpha_{adj}$BH | $H_0$ seqB | $H_0$ BH |
| SW | M | 0.513 | 0.0500 | 0.0500 | Retained | Retained |
| | P | 0.229 | 0.0250 | 0.0333 | Retained | Retained |
| | M × P | 0.227 | 0.0167 | 0.0167 | Retained | Retained |
| SL | M | 0.248 | 0.0500 | 0.0500 | Retained | Retained |
| | P | 0.041 | 0.0167 | 0.0167 | Retained | Retained |
| | M × P | 0.092 | 0.0250 | 0.0333 | Retained | Retained |
| SWV | M | 0.135 | 0.0167 | 0.0167 | Retained | Retained |
| | P | 0.495 | 0.0250 | 0.0333 | Retained | Retained |
| | M × P | 0.927 | 0.0500 | 0.0500 | Retained | Retained |
| SLV | M | 0.339 | 0.0500 | 0.0500 | Retained | Retained |
| | P | 0.128 | 0.0167 | 0.0167 | Retained | Retained |
| | M × P | 0.160 | 0.0250 | 0.0333 | Retained | Retained |

TABLE B

| | Effect | p value | $\alpha_{adj}$SeqB | $\alpha_{adj}$BH | $H_0$ seqB | $H_0$ BH |
|---|---|---|---|---|---|---|
| SW | M | 0.875 | 0.0500 | 0.0500 | Retained | Retained |
| | P | 0.002 | 0.0167 | 0.0167 | Rejected | Rejected |
| | M × P | 0.875 | 0.0250 | 0.0333 | Retained | Retained |
| SL | M | 0.534 | 0.0500 | 0.0500 | Retained | Retained |
| | P | <0.001 | 0.0167 | 0.0167 | Rejected | Rejected |
| | M × P | 0.495 | 0.0250 | 0.0333 | Retained | Retained |
| SWV | M | 0.056 | 0.0167 | 0.0167 | Retained | Retained |
| | P | 0.325 | 0.0250 | 0.0333 | Retained | Retained |
| | M × P | 0.982 | 0.0500 | 0.0500 | Retained | Retained |
| SLV | M | 0.744 | 0.0500 | 0.0500 | Retained | Retained |
| | P | 0.014 | 0.0167 | 0.0167 | Rejected | Rejected |
| | M × P | 0.653 | 0.0250 | 0.0333 | Retained | Retained |

Results from the sequential Bonferroni (seqB) and Benjamini-Hochberg (BH) procedures for the data in FIGS. 4 and 5 are presented below in Table C (for positive feedback gains) and Table D (for negative feedback gains).

In Tables C and D, the following notations are used: M: magnitude, P: Phase, M×P: the interaction between Magnitude and Phase. $\alpha_{adj}$seqB=the adjusted alpha level with the sequential Bonferroni procedure; $\alpha_{adj}$BH=the adjusted alpha level with the Benjamini-Hochberg procedure; $H_0$seqB=evaluation of the null hypotheses with the sequential Bonferroni procedure; $H_0$BH=evaluation of the null hypotheses with the Benjamini-Hochberg procedure.

TABLE C

| | | Effect | p value | $\alpha_{adj}$SeqB | $\alpha_{adj}$BH | $H_0$ seqB | $H_0$ BH |
|---|---|---|---|---|---|---|---|
| C7 | | M | 0.647 | 0.0250 | 0.0333 | Retained | Retained |
| Step-step range | | P | 0.854 | 0.0500 | 0.0500 | Retained | Retained |
| | | M × P | 0.054 | 0.0167 | 0.0167 | Retained | Retained |
| C7 | | M | 0.056 | 0.0167 | 0.0167 | Retained | Retained |
| ML | | P | 0.294 | 0.0250 | 0.0333 | Retained | Retained |
| RMS | | M × P | 0.369 | 0.0500 | 0.0500 | Retained | Retained |

TABLE D

| | | Effect | p value | $\alpha_{adj}$SeqB | $\alpha_{adj}$BH | $H_0$ seqB | $H_0$ BH |
|---|---|---|---|---|---|---|---|
| C7 | | M | 0.054 | 0.0167 | 0.0167 | Retained | Retained |
| Step-step range | | P | 0.125 | 0.0250 | 0.0333 | Retained | Retained |
| | | M × P | 0.867 | 0.0500 | 0.0500 | Retained | Retained |
| C7 | | M | 0.113 | 0.0167 | 0.0167 | Retained | Retained |
| ML | | P | 0.552 | 0.0500 | 0.0500 | Retained | Retained |
| RMS | | M × P | 0.476 | 0.0250 | 0.0333 | Retained | Retained |

The disclosure of each of the following references is incorporated herein by reference in its entirety.

REFERENCES

Anson, E., Rosenberg, R., Agada, P., Kiemel, T., & Jeka, J. (2013). Does visual feedback during walking result in similar improvements in trunk control for young and older healthy adults? Journal of Neuroengineering and Rehabilitation, 10, 110.

Cowan, N. J., & Fortune, E. S. (2007). The critical role of locomotion mechanics in decoding sensory systems. Journal of Neuroscience, 27, 1123-1128.

Cramer, A. O., van Ravenzwaaij, D., Matzke, D., Steingroever, H., Wetzels, R., Grasman, R. P., & Wagenmakers, E. J. (2016). Hidden multiplicity in exploratory multiway ANOVA: Prevalence and remedies. Psychonomic Bulletin & Review, 23, 640-647.

Dingwell, J. B., & Cusumano, J. P. (2010). Re-interpreting detrended fluctuation analyses of stride-to-stride variability in human walking. Gait & Posture, 32, 348-353. Franz, J. R., Francis, C., Allen, M., & Thelen, D. G. (2016). Visuomotor entrainment and the frequency-dependent response of walking balance to perturbations. IEEE Transactions on Neural Systems and Rehabilitation Engineering, 25, 1135-1142.

Grabiner, M. D., Bareither, M. L., Gatts, S., Marone, J., & Troy, K. L. (2012). Task-specific training reduces trip-related fall risk in women. Medicine & Science in Sports & Exercise, 44, 2410-2414.

Hayhoe, M., Gillam, B., Chajka, K., & Vecellio, E. (2009). The role of binocular vision in walking. Visual Neuroscience, 26, 73-80.

Hilliard, M. J., Martinez, K. M., Janssen, I., Edwards, B., Mille, M. L., Zhang, Y., & Rogers, M. W. (2008). Lateral balance factors predict future falls in community-living older adults. Archives of Physical Medicine and Rehabilitation, 89, 1708-1713.

Hurt, C. P., Rosenblatt, N., Crenshaw, J. R., & Grabiner, M. D. (2010). Variation in trunk kinematics influences variation in step width during treadmill walking by older and younger adults. Gait & Posture, 31, 461-464.

Keppel, G., & Wickens, T. D. (2004). Effect Size, Power, and Sample Size. In Design and Analysis: a Researcher's Handbook, 4th Edition (Vol. 5, pp. 159-179). Upper Saddle River, N.J.: Pearson Prentice Hall.

Kiemel, T., Zhang, Y. F., & Jeka, J. J. (2011). Identification of neural feedback for upright stance in humans: stabilization rather than sway minimization. Journal of Neuroscience, 31, 15144-15153.

Logan, D., Kiemel, T., Dominici, N., Cappellini, G., Ivanenko, Y., Lacquaniti, F., & Jeka, J. J. (2010). The many roles of vision during walking. Experimental Brain Research, 206, 337-350.

McAndrew, P. M., Dingwell, J. B., & Wilken, J. M. (2010). Walking variability during continuous pseudo-random oscillations of the support surface and visual field. Journal of Biomechanics, 43, 1470-1475.

O'Connor, S. M., & Kuo, A. D. (2009). Direction-dependent control of balance during walking and standing. Journal of Neurophysiology, 102, 1411-1419. Patla, A. E. (1998). How is human gait controlled by vision? Ecological Psychology, 10, 287-302.

Patton, J. L., Wei, Y. J., Bajaj, P., & Scheidt, R. A. (2013). Visuomotor learning enhanced by augmenting instantaneous trajectory error feedback during reaching. PLoS One, 8, e46466.

Peterka, R. J. (2002). Sensorimotor integration in human postural control. Journal of Neurophysiology, 88, 1097-1118.

Peterka, R. J., & Loughlin, P. J. (2004). Dynamic regulation of sensorimotor integration in human postural control. Journal of Neurophysiology, 91, 410-423.

Peterson, S. M., Rios, E., & Ferris, D. P. (2018). Transient visual perturbations boost short-term balance learning in virtual reality by modulating electrocortical activity. Journal of Neurophysiology, 120(4), 1998-2010. https://doi.org/10.1152/jn.00292.2018.

Qiao, M., Feld, J. A., & Franz, J. R. (2018). Aging effects on leg joint variability during walking with balance perturbations. Gait & Posture, 62, 27-33.

Qiao, M., Truong, K. N., & Franz, J. R. (2018). Does local dynamic stability during unperturbed walking predict the response to balance perturbations? An examination across age and falls history. Gait & Posture, 62, 80-85.

Richards, J. T., Selgrade, B. P., Qiao, M., Plummer, P., Wikstrom, E. A., & Franz, J. R. (2019). Time-dependent tuning of balance control and aftereffects following optical flow perturbation training in older adults. Journal of Neuroengineering and Rehabilitation, 16, 81.

Ros, I. G., & Biewener, A. A. (2016). Optic flow stabilizes flight in ruby-throated hummingbirds. Journal of Experimental Biology, 219, 2443-2448.

Sinitksi, E. H., Terry, K., Wilken, J. M., & Dingwell, J. B. (2012). Effects of perturbation magnitude on dynamic stability when walking in destabilizing environments. Journal of Biomechanics, 45, 2084-2091.

Terry, K., Sinitski, E. H., Dingwell, J. B., & Wilken, J. M. (2012). Amplitude effects of medio-lateral mechanical and visual perturbations on gait. Journal of Biomechanics, 45, 1979-1986.

Thompson, J. D., & Franz, J. R. (2017). Do kinematic metrics of walking balance adapt to perturbed optical flow? Human Movement Science, 54, 34-40.

Tseng, Y. W., Diedrichsen, J., Krakauer, J. W., Shadmehr, R., & Bastian, A. J. (2007). Sensory prediction errors drive cerebellum-dependent adaptation of reaching. Journal of Neurophysiology, 98, 54-62.

Warren, W. H., & Hannon, D. J. (1988). Direction of self-motion is perceived from optical-flow. Nature, 336, 162-163.

Warren, W. H., Kay, B. A., & Yilmaz, E. H. (1996). Visual control of posture during walking: Functional specificity. Journal of Experimental Psychology. Human Perception and Performance, 22, 818-838.

Wilkie, R. M., Kountouriotis, G. K., Merat, N., & Wann, J. P. (2010). Using vision to control locomotion: Looking where you want to go. Experimental Brain Research, 204, 539-547.

Wolpert, D. M., & Miall, R. C. (1996). Forward models for physiological motor control. Neural Networks, 9, 1265-1279.

Zeni, J. A., Jr., Richards, J. G., & Higginson, J. S. (2008). Two simple methods for determining gait events during treadmill and overground walking using kinematic data. Gait & Posture, 27, 710-714.

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A method comprising:
   displaying a dynamic virtual environment defined by an optical flow;
   obtaining position data of an anatomical portion of a subject that is virtually traversing the dynamic virtual environment;
   using the position data to determine a mediolateral displacement measurement of the subject;
   utilizing the mediolateral displacement measurement to define feedback control loop data;
   establishing an augmented visual error that dynamically adjusts the dynamic virtual environment, wherein the augmented visual error is based on the feedback control loop data and a predefined visual gain factor, wherein the augmented visual error defines a difference between a virtual perception of trunk motion of the subject and an actual trunk motion of the subject; and
   adjusting the optical flow of the dynamic virtual environment by using the augmented visual error.

2. The method of claim 1 wherein the dynamic virtual environment includes a virtual hallway.

3. The method of claim 1 wherein a foreground mediolateral position of the dynamic virtual environment is adjusted by the augmented visual error.

4. The method of claim 1 wherein the mediolateral displacement measurement is based on a difference of a mediolateral position of the dynamic virtual environment and a mediolateral position marker of the subject.

5. The method of claim 4 wherein the anatomical portion of the subject corresponds to at least one of a seventh cervical vertebrae of the subject, a global head position of the subject, and a global trunk position of the subject.

6. The method of claim 1 further comprising moving a foreground of the dynamic virtual environment based on the feedback control loop data and the augmented visual error by a value of G.

7. A system comprising:
   a display device configured to display a dynamic virtual environment defined by an optical flow;
   at least one position sensor device configured to obtain position data of an anatomical portion of a subject that is virtually traversing the dynamic virtual environment; and
   a system controller device configured to use the position data to determine a mediolateral displacement measurement of the subject, utilize the mediolateral displacement measurement to define feedback control loop data, establish an augmented visual error that dynamically adjusts the dynamic virtual environment, wherein the augmented visual error is based on the feedback control loop data and a predefined visual gain factor, wherein the augmented visual error defines a difference between a virtual perception of trunk motion of the subject and an actual trunk motion of the subject, and adjust the optical flow of the dynamic virtual environment by using the augmented visual error.

8. The system of claim 7 wherein the dynamic virtual environment includes a virtual hallway.

9. The system of claim 7 wherein a foreground mediolateral position of the dynamic virtual environment is adjusted by the augmented visual error.

10. The system of claim 7 wherein the mediolateral displacement measurement is based on a difference of a mediolateral position of the dynamic virtual environment and a mediolateral position marker of the subject.

11. The system of claim 10 wherein the anatomical portion of the subject corresponds to at least one of a seventh cervical vertebrae of the subject, a global head position of the subject, and a global trunk position of the subject.

12. The system of claim 7 wherein the system controller device is further configured to move a foreground of the dynamic virtual environment based on the feedback control loop data and the augmented visual error by a value of G.

13. A non-transitory computer readable medium having stored thereon executable instructions that when executed by a processor of a computer control the computer to perform steps comprising:
   displaying a dynamic virtual environment defined by an optical flow;

obtaining position data of an anatomical portion of a subject that is virtually traversing the dynamic virtual environment;

using the position data to determine a mediolateral displacement measurement of the subject;

utilizing the mediolateral displacement measurement to define feedback control loop data;

establishing an augmented visual error that dynamically adjusts the dynamic virtual environment, wherein the augmented visual error is based on the feedback control loop data and a predefined visual gain factor, wherein the augmented visual error defines a difference between a virtual perception of trunk motion of the subject and an actual trunk motion of the subject; and adjusting the optical flow of the dynamic virtual environment by using the augmented visual error.

14. The non-transitory computer readable medium of claim 13 wherein the dynamic virtual environment includes a virtual hallway.

15. The non-transitory computer readable medium of claim 13 wherein a foreground mediolateral position of the dynamic virtual environment is adjusted by the augmented visual error.

16. The non-transitory computer readable medium of claim 13 wherein the mediolateral displacement measurement is based on a difference of a mediolateral position of the dynamic virtual environment and a mediolateral position marker of the subject.

17. The non-transitory computer readable medium of claim 16 wherein the anatomical portion of the subject corresponds to at least one of a seventh cervical vertebrae of the subject, a global head position of the subject, and a global trunk position of the subject.

* * * * *